United States Patent [19]

Bourzat et al.

[11] 4,164,579
[45] Aug. 14, 1979

[54] HYDROXYTHIAZOLIDINE-2-THIONES

[75] Inventors: Jean D. Bourzat, Paris; Daniel Farge, Thiais; André Léger, Paris; Gérard Ponsinet, Sucy-en-Brie, all of France

[73] Assignee: Rhone-Poulenc Industries, Paris, France

[21] Appl. No.: 906,599

[22] Filed: May 16, 1978

[30] Foreign Application Priority Data

May 17, 1977 [FR] France .................. 77 15072
Apr. 25, 1978 [FR] France .................. 78 12187

[51] Int. Cl.² .............. C07D 213/71; C07D 409/04; A61K 31/44
[52] U.S. Cl. ............................ 424/263; 546/280; 546/305
[58] Field of Search ............ 260/294.8 D, 294.8 E; 424/263; 546/280, 305

[56] References Cited
U.S. PATENT DOCUMENTS 3,726,880  4/1973  Capps ..................... 546/305
3,761,485  9/1973  Erdelyi et al. .............. 546/305

Primary Examiner—Alan L. Rotman
Attorney, Agent, or Firm—Stevens, Davis, Miller & Mosher

[57] ABSTRACT

Compounds of the formula:

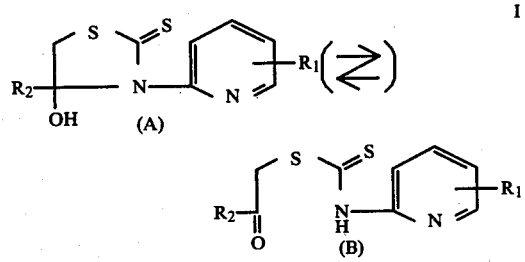

wherein $R_1$ represents alkyl of 1 through 4 carbon atoms in the 4-, 5- or 6-position of the pyridyl radical, and $R_2$ represents hydrogen or alkyl of 1 through 4 carbon atoms, are useful as anti-ulcer agents.

18 Claims, No Drawings

HYDROXYTHIAZOLIDINE-2-THIONES

This invention relates to new 4-hydroxythiazolidine-2-thione derivatives, a process for their preparation and pharmaceutical compositions containing them.

The 4-hydroxythiazolidine-2-thione derivatives of the present invention are those compounds of general formula:

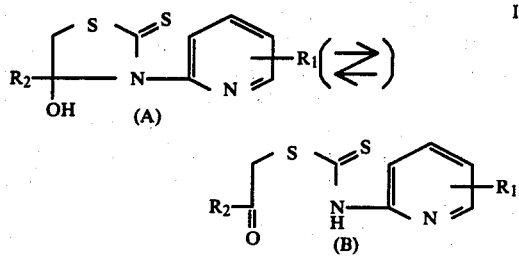

wherein $R_1$ represents a straight- or branched-chain alkyl radical containing 1 to 4 carbon atoms in the 4-, 5- or 6-position of the pyridyl radical, and $R_2$ represents a hydrogen atom or a straight- or branched-chain alkyl radical containing 1 to 4 carbon atoms.

The products according to the invention can be in one of the forms I(A) or I(B) or an equilibrium mixture of these two forms, depending on internal parameters (especially the radicals $R_1$ and $R_2$) or external parameters (especially the presence of a solvent), as will be shown hereafter.

This existence of the two forms I(A) and I(B) of the 4-hydroxythiazolidine-2-thiones is well known and forms the subject of various publications, especially those by R. W. Lamon et al., J. Org. Chem., 29, 2146 (1964) and J. Het. Chem., 4, 349 (1967).

General formula I(A) generally corresponds to the preponderant form, in the crystalline state, of the products in which $R_1$ is as hereinbefore defined, and $R_2$ represents a hydrogen atom, or an alkyl radical containing 1 to 4 carbon atoms, the carbon atoms of which are only primary or secondary.

General formula I(B) generally corresponds to the preponderant form, in the crystalline state, of the products in which $R_1$ is as hereinbefore defined and $R_2$ represents the tertiary butyl radical.

According to a feature of the present invention, the compounds of general formula I are prepared by reacting an α-halogenoketone, (which can be prepared in situ), of the general formula:

$$R_2-CO-CH_2-X \qquad II$$

(wherein $R_2$ is as hereinbefore defined and X represents a halogen, preferably bromine or chlorine, atom) with a dithiocarbamate of the general formula:

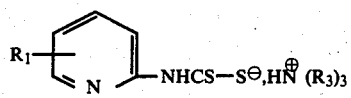

wherein $R_1$ is as hereinbefore defined, and the symbols $R_3$ each represent an alkyl radical containing 1 to 4 carbon atoms, which may be the same or different.

The reaction is generally carried out in an organic solvent (for example dimethylformamide or acetonitrile), in water or in an aqueous-organic medium (for example, in a mixture of water and dimethylformamide or water and acetonitrile) at a temperature between −10° and +50° C.

The dithiocarbamates of general formula III can be obtained, in accordance with the method described by E. B. Knott, J. Chem. Soc., 1644–9 (1956), by the action of carbon disulphide, in the presence of a tertiary amine, on a 2-aminopyridine of the general formula:

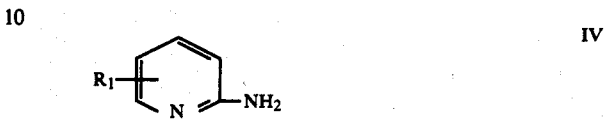

wherein $R_1$ is as hereinbefore defined, or in accordance with the method described by D. B. Capps in the specification of U.S. Pat. No. 3,726,880.

The α-halogenoketones of general formula II can be prepared by applying various general methods described in the literature.

The compounds of general formula I can optionally be purified by physical methods such as crystallisation or chromatography.

The compounds of the present invention possess pharmacological properties which justify their use as anti-ulcer agents.

The compounds have shown themselves to be active in the rat at doses between 10 and 100 mg/kg animal body weight p.o. according to the technique of Rossi et al, C.R. Soc. Biol., 150, 2 124 and certain of them have been shown to be active at doses of from 5 to 100 mg/kg animal body weight p.o in the technique of Shay et al., Gastroenterology, 5, 43 (1945).

Their acute toxicity in mice is between 300 and 900 mg/kg animal body weight when administered orally or greater than the aforementioned higher dosage.

Preferred compounds of the present invention are those of general formula I wherein $R_1$ represents the methyl or ethyl radical.

The following non-limitative Examples illustrate the preparation of compounds of the present invention.

EXAMPLE 1

A 50% (by weight) aqueous solution of chloroacetaldehyde (28.4 g) is added, at a maximum temperature of 30° C., to a solution of triethylammonium (6-methylpyrid-2-yl)-dithiocarbamate (51.5 g) in distilled water (225 cc). The reaction is continued for 2 hours at 20°–30° C. The resulting crystals are separated by filtration, washed five times with distilled water (total 125 cc) and dried in air at 20° C. The product obtained (37.0 g; m.p. 127° C.) is dissolved in a mixture of chloroform (600 cc) and diethyl ether (300 cc); the organic solution is washed three times with distilled water (total 450 cc), dried over sodium sulphate, treated with decolorising charcoal (1 g) and evaporated. The crystals obtained (34.0 g; m.p. 128° C.) are dissolved in boiling ethanol (240 cc). After 2 hours cooling at 2° C., the resulting crystals are separated by filtration, washed twice with ice-cold ethanol (total 30 cc) and dried under reduced pressure (0.1 mm.Hg) at 50° C. 4-Hydroxy-3-(6-methylpyrid-2-yl)-thiazolidine-2-thione (28.8 g), melting at 128° C., is thus obtained.

The triethylammonium (6-methylpyrid-2-yl)dithiocarbamate is prepared by the method described by E. B. Knott, J. Chem. Soc., 1644–49 (1956).

EXAMPLE 2

Chloroacetone (13.9 cc) is added to a solution of triethylammonium (6-methylpyrid-2-yl)dithiocarbamate (50.0 g) in dimethylformamide (250 cc) at a temperature between 15 and 23° C. The reaction is continued for 3 hours at 20°–23° C. After filtration and evaporation of the dimethylformamide under reduced pressure (0.1 mm.Hg) at 45° C., the residual oil is dissolved in ethyl acetate (500 cc); the organic solution is washed with distilled water (100 cc), dried over sodium sulphate, treated with decolorising charcoal (2 g) and evaporated. The crystals obtained (38.0 g; m.p. 150°–153° C.) are dissolved in boiling ethanol (520 cc). After 2 hours cooling at 2° C., the resulting crystals are separated by filtration, washed twice with ice-cold ethanol (total 80 cc) and dried under reduced pressure (0.1 mm.Hg) at 45° C. 4-Hydroxy-4-methyl-3-(6-methylpyrid-2-yl)-thiazolidine-2-thione (24.9 g), melting at 156° C., is obtained.

EXAMPLE 3

The procedure of Example 1 is followed but starting with triethylammonium (6-methylpyrid-2-yl)dithiocarbamate (71.0 g) and 1-chlorobutan-2-one (26.6 g) in distilled water (300 cc) at 20° C. The reaction is carried out for 3 hours at 20° C. After recrystallisation of the product from ethanol (250 cc), there is obtained 4-ethyl-4-hydroxy-3-(6-methylpyrid-2-yl)-thiazolidine-2-thione (45.0 g) melting at 118° C.

1-Chlorobutan-2-one (b.p. 119°–122° C./760 mm.Hg) is prepared according to the method described by P. J. Ashworth et al, J. Chem. Soc. 4633 (1957).

EXAMPLE 4

1-Chloropentan-2-one (12.1 g) is added to a suspension of triethylammonium (6-methylpyrid-2-yl)dithiocarbamate (28.5 g) in anhydrous acetonitrile (200 cc) at a temperature between 15° and 25° C. The reaction is continued for 2 hours at 20°–25° C. The insoluble triethylamine hydrochloride is removed by filtration and washed twice with diethyl ether (60 cc. total). The solvents are evaporated under reduced pressure (20 mm.Hg) at 40° C. The residual oil is dissolved in a mixture of diethyl ether (100 cc) and methylene chloride (50 cc); the organic solution is washed twice with distilled water (total 100 cc), dried over sodium sulphate and evaporated. The crystals obtained (25.4 g; m.p. about 70° C.) are dissolved in boiling cyclohexane (500 cc) and the boiling solution is filtered. After cooling for 1 hour at about 10° C., the resulting crystals are separated by filtration, washed twice with cyclohexane (total 120 cc) cooled to 10° C., and dried under reduced pressure (0.1 mm.Hg) at 40° C. 4-Hydroxy-3-(6-methylpyrid-2-yl)-4-propylthiazolidine-2-thione (21.6 g), melting at 83° C., is thus obtained.

1-Chloropentan-2-one (b.p. 65°–67° C./30 mm.Hg) is prepared according to the method described by R. D. Haworth et al, J. Chem. Soc., 3617 (1954).

EXAMPLE 5

The procedure of Example 4 is followed starting with triethylammonium (6-methylpyrid-2-yl)dithiocarbamate (18.5 g) and 1-chloro-3-methylbutan-2-one (7.9 g) in anhydrous acetonitrile (200 cc) at a temperature between 15° and 20° C. The reaction is continued for 2 hours at 20° C. After recrystallisation of the product from a mixture of diisopropyl ether (340 cc) and acetonitrile (90 cc), 4-hydroxy-4-isopropyl-3-(6-methylpyrid-2-yl)-thiazolidine-2-thione (10.1 g), melting at 140° C., is obtained.

1-Chloro-3-methylbutan-2-one (b.p. 62° C./25 mm.Hg) is prepared according to the method described by R. Justoni and M. Teruzzi, Gazz. Chim. Ital., 78, 166 (1948).

EXAMPLE 6

The procedure of Example 4 is followed but starting with triethylammonium (6-methylpyrid-2-yl)dithiocarbamate (34.2 g) and 1-chlorohexan-2-one (16.1 g) in anhydrous acetonitrile (320 cc) at a temperature between 20° and 25° C. The reaction is continued for 2 hours at 20° to 25° C. After recrystallisation of the product from cyclohexane (600 cc), 4-butyl-4-hydroxy-3-(6-methylpyrid-2-yl)-thiazolidine-2-thione (28.3 g), melting at 80° C., is obtained.

1-Chlorohexan-2-one (b.p. 80°–81° C./25 mm.Hg) is prepared according to the method described by H. Erlenmeyer and J. P. Jong, Helv. Chim. Acta, 32, 35 (1949).

EXAMPLE 7

The procedure of Example 4 is followed but starting with triethylammonium (6-methylpyrid-2-yl)dithiocarbamate (28.5 g) and 1-chloro-4-methylpentan-2-one (13.4 g) in anhydrous acetonitrile (200 cc) at a temperature between 20 and 25° C. The reaction is continued for 2 hours at 20°–25° C. After recrystallisation of the product from diisopropyl ether (390 cc) and filtration of the boiling solution, there is obtained 4-hydroxy-4-isobutyl-3-(6-methylpyrid-2-yl)-thiazolidine-2-thione (16.8 g) melting at 95° C.

When the product is examined by infra-red spectroscopy in carbon tetrachloride solution, there is observed about 5 to 10% of 4-methyl-2-oxopentyl (6-methylpyrid-2-yl)dithiocarbamate (carbonyl band at 1710 cm$^{-1}$). This form does not appear when the product is examined between plates in Vaseline (a registered Trade Mark).

1-Chloro-4-methylpentan-2-one (b.p. 72°–73° C./25 mm.Hg) is prepared according to the method described by F. Asinger et al, Ann. Chem., 672, 156 (1964).

EXAMPLE 8

1-Bromo-3,3-dimethylbutan-2-one (40.0 g) is added to a suspension of triethylammonium (6-methylpyrid-2-yl)dithiocarbamate (64.0 g) in anhydrous acetonitrile (600 cc) at a maximum temperature of 20° C. The reaction is continued for 2 hours at 20° C. The insoluble hydrobromide of triethylamine is removed by filtration and washed with acetonitrile (50 cc). The organic phases are combined and evaporated under reduced pressure (20 mm.Hg) at 45° C. The residual oil is treated with diethyl ether (1200 cc). After 1 hour at 20° C., the ethereal solution is filtered, washed twice with distilled water (total 400 cc), dried over sodium sulphate and evaporated. The product obtained (60.0 g) is dissolved in boiling diisopropyl ether (870 cc) and the boiling solution is filtered. After 1 hour's cooling at 2° C., the resulting crystals are filtered off, washed twice with ice-cold diisopropyl ether (total 100 cc) and dried under reduced pressure (0.1 mm.Hg) at 40° C. to give 3,3-dimethyl-2-oxobutyl (6-methylpyrid-2-yl)dithiocarbamate (44.1 g) melting at 80° C.

EXAMPLE 9

The procedure of Example 1 is followed but starting with triethylammonium (6-ethylpyrid-2-yl)dithiocarbamate (43.5 g) and chloroacetone (13.4 g) in distilled water (220° C.) at a maximum temperature of 30° C. The reaction is continued for 3 hours at 20°-30° C. After recrystallisation of the product from ethanol (120 cc), 3-(6-ethylpyrid-2-yl)-4-hydroxy-4-methylthiazolidine-2-thione (25.5 g), melting at 122° C., is obtained.

Triethylammonium (6-ethylpyrid-2-yl)dithiocarbamate employed as starting material can be prepared in the following way:

A solution of carbon disulphide (17.5 cc) in anhydrous acetonitrile (19.5 cc) is added to a solution of 2-amino-6-ethylpyridine (27.0 g) in anhydrous triethylamine (60 cc) at a temperature of 25° C. After 20 hours stirring at 20° C., anhydous diethyl ether (250 cc) is added. After cooling for 1 hour at 2° C., the resulting crystals are filtered off, washed three times with anhydrous diethyl ether (240 cc) and dried under reduced pressure (20 mm.Hg) at 20° C. to give triethylammonium (6-ethylpyrid-2-yl)dithiocarbamate (42.0 g) melting at 75° C.

2-Amino-6-ethylpyridine is prepared according to the method described by S. J. Childress and J. V. Scusi, J. Org. Chem., 23, 68 (1958).

EXAMPLE 10

The procedure of Example 4 is followed but starting with triethylammonium (6-ethylpyrid-2-yl)dithiocarbamate (72.0 g) and 1-chlorobutan-2-one (25.5 g) in anhydrous acetonitrile (400 cc) at a maximum temperature of 25° C. The reaction is continued for 4 hours at 20°-25° C. The product is purified by chromatography over silica (470 g; 0.063-0.200 mm) contained in a column 3.8 cm in diameter, eluting with chloroform (5 liters). The chromatographed product (43.0 g) is recrystallised from ethanol (120 cc) to give 4-ethyl-3-(6-ethylpyrid-2-yl)-4-hydroxythiazolidine-2-thione (37.2 g) melting at 84° C.

EXAMPLE 11

The procedure of Example 2 is followed but starting with triethylammonium (4-methylpyrid-2-yl)dithiocarbamate (100.0 g) and chloroacetone (32.3 g) in dimethylformamide (450 cc) at a temperature between 10° and 15° C. The reaction is continued for 90 minutes at 15°-20° C. After recrystallisation of the product from a mixture of ethanol (250 cc) and diisopropyl ether (250 cc), 4-hydroxy-4-methyl-3-(4-methylpyrid-2-yl)-thiazolidine-2-thione (49.0 g), melting at 119° C., is obtained.

Triethylammonium (4-methylpyrid-2-yl)dithiocarbamate (m.p. 100° C.) is prepared according to the method described by E. B. Knott, J. Chem. Soc., 1644-49 (1956).

EXAMPLE 12

The procedure of Example 2 is followed but starting with triethylammonium (5-methylpyrid-2-yl)dithiocarbamate (75.0 g) and chloroacetone (20.9 cc) in dimethylformamide (340 cc) at a maximum temperature of 20° C. The reaction is continued for 16 hours at 20° C. After recrystallisation of the product from a mixture of ethanol (100 cc) and diisopropyl ether (150 cc), 4-hydroxy-4-methyl-3-(5-methylpyrid-2-yl)thiazolidine-2-thione (45.1 g), melting at 113° C., is obtained.

Triethylammonium (5-methylpyrid-2-yl)dithiocarbamate (m.p. 115° C.) is prepared according to the method described in the Specification of German Pat. No. 2,508,891.

The present invention includes within its scope pharmaceutical compositions which comprise, as active ingredient, at least one of the compounds of general formula I in association with one or more compatible and pharmaceutically acceptable carriers. The invention includes especially such preparations made up for oral, parenteral or rectal administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents.

Compositions according to the invention for parenteral administration include sterile aqueous or non-aqueous solutions, suspensions or emulsions.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. The compositions are particularly useful in human therapy for the treatment of medicinal and other gastritis and gastralgias and the treatment of ulcers (gastric or duodenal ulcers and peptic ulcers). In human therapy the compositions when administered orally to an adult should generally give doses between 50 mg and 1000 mg of active substance per day. In general the physician will decide the posology considered appropriate, taking into account the age and weight and other factors intrinsic to the patient being treated.

The following Example illustrates pharmaceutical compositions according to the invention.

EXAMPLE 13

Tablets having the following composition are prepared in accordance with the usual technique:

| | |
|---|---|
| 4-ethyl-3-(6-ethylpyrid-2-yl)-4-hydroxythiazolidine-2-thione | 50 mg |
| starch | 15 mg |
| precipitated silica | 9.5 mg |
| magnesium stearate | 0.5 mg |

We claim:

1. A compound of the formula:

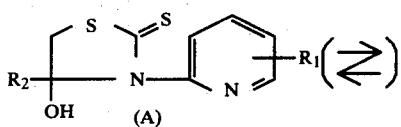

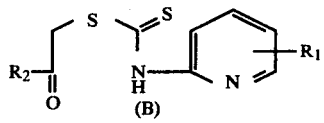

wherein $R_1$ represents alkyl of 1 through 4 carbon atoms in the 4-, 5- or 6-position of the pyridyl radical, and $R_2$ represents hydrogen or alkyl of 1 through 4 carbon atoms.

2. A compound according to claim 1 which, in predominant form in the crystalline state, corresponds to formula I(A) wherein $R_1$ is as defined in claim 1, and $R_2$ represents hydrogen or alkyl of 1 through 4 carbon atoms, the carbon atoms of which are only primary or secondary.

3. A compound according to claim 1 which, in predominant form in the crystalline state, corresponds to formula I(B) wherein $R_1$ is as defined in claim 1, and $R_2$ represents tertiary butyl.

4. A compound according to claim 1 wherein $R_1$ represents methyl or ethyl.

5. The compound according to claim 1 which is 4-hydroxy-3-(6-methylpyrid-2-yl)-thiazolidine-2-thione.

6. The compound according to claim 1 which is 4-hydroxy-4-methyl-3-(6-methylpyrid-2-yl)-thiazolidine-2-thione.

7. The compound according to claim 1 which is 4-ethyl-4-hydroxy-3-(6-methylpyrid-2-yl)-thiazolidine-2-thione.

8. The compound according to claim 1 which is 4-hydroxy-3-(6-methylpyrid-2-yl)-4-propylthiazolidine-2-thione.

9. The compound according to claim 1 which is 4-hydroxy-4-isopropyl-3-(6-methylpyrid-2-yl)-thiazolidine-2-thione.

10. The compound according to claim 1 which is 4-butyl-4-hydroxy-3-(6-methylpyrid-2-yl)-thiazolidine-2-thione.

11. The compound according to claim 1 which is 4-hydroxy-4-isobutyl-3-(6-methylpyrid-2-yl)-thiazolidine-2-thione.

12. The compound according to claim 1 which is 3-(6-ethylpyrid-2-yl)-4-hydroxy-4-methylthiazolidine-2-thione.

13. The compound according to claim 1 which is 4-ethyl-3-(6-ethylpyrid-2-yl)-4-hydroxythiazolidine-2-thione.

14. The compound according to claim 1 which is 4-hydroxy-4-methyl-3-(4-methylpyrid-2-yl)-thiazolidine-2-thione.

15. The compound according to claim 1 which is 4-hydroxy-4-methyl-3-(5-methylpyrid-2-yl)-thiazolidine-2-thione.

16. The compound according to claim 1 which is 3,3-dimethyl-2-oxobutyl (6-methylpyrid-2-yl)dithiocarbamate.

17. A pharmaceutical composition useful for the treatment of gastritis, gastralgias, and gastric, duodenal, and peptic ulcers which comprises, as active ingredient, an effective amount of a compound claimed in claim 1, 2, 3, 4, 5, 6, 7, 8, 9, 10, 11, 12, 13, 14, 15 and 16 in association with a significant amount of at least one compatible and pharmaceutically-acceptable carrier.

18. A method for the treatment of gastric, duodenal, and peptic ulcers which comprises administering orally to an adult patient between 50 and 1000 mg. per day of a compound claimed in claim 1, 2, 3, 4, 5, 6, 7, 8, 9, 10, 11, 12, 13, 14, 15 or 16.

* * * * *